US011564933B2

(12) United States Patent
Dudley et al.

(10) Patent No.: US 11,564,933 B2
(45) Date of Patent: Jan. 31, 2023

(54) METHODS OF TREATING TESTOSTERONE DEFICIENCY

(71) Applicant: Tolmar, Inc., Fort Collins, CO (US)

(72) Inventors: Robert E. Dudley, Murfreesboro, TN (US); Theodore Danoff, Philadelphia, PA (US)

(73) Assignee: Tolmar, Inc., Fort Collins, CO (US)

( * ) Notice: Subject to any disclaimer, the term of this patent is extended or adjusted under 35 U.S.C. 154(b) by 0 days.

(21) Appl. No.: 16/382,835

(22) Filed: Apr. 12, 2019

(65) Prior Publication Data
US 2020/0323880 A1    Oct. 15, 2020

(51) Int. Cl.
*A61K 31/568* (2006.01)
*A61K 9/00* (2006.01)

(52) U.S. Cl.
CPC .......... *A61K 31/568* (2013.01); *A61K 9/0053* (2013.01)

(58) Field of Classification Search
CPC ..... A61K 31/56; A61K 31/568; A61K 9/0053
See application file for complete search history.

(56) References Cited

U.S. PATENT DOCUMENTS 6,652,880 B1 * 11/2003 Aylwin ................. A61K 9/1075
424/451
2012/0148675 A1 * 6/2012 Chickmath ............ A61K 9/205
424/489

FOREIGN PATENT DOCUMENTS

WO    WO-2011129812 A1 * 10/2011 ........... A61K 31/568

OTHER PUBLICATIONS

Reckelhoff et al., Hypertension, 1998;31[part2]:435-439 (Year: 1998).*
Dalmasso, C. et al., "Cardiovascular and Metabolic Consequences of Testosterone Supplements in Young and Old Male Spontaneously Hypertensive Rats: Implications for Testosterone Supplements in Men", J Am Heart Assoc., 1-10, (2017).
Fernandez-Balsells et al., "Adverse Effects of Testosterone Therapy in Adult Men: A Systematic Review and Meta-Analysis", J. Clin. Endocrinol. Metab., 95(6):2560-2575, (2010).
Velho, I. et al., "Effects of Testosterone Therapy on BMI, Blood Pressure, and Laboratory Profile of Transgender Men: A Systematic Review", Andrology, 5:881-888, (2017).
Ohlsson, C. et al., "High Serum Testosterone is Associated with Reduced Risk of Cardiovascular Events in Elderiy Men", JACC 58(16):1674-1681 (2011).
Vikan, T. et al., "Endogenous Sex Hormones and the Prospective Association with Cardiovascular Disease and Mortality in Men. The Tromø Study.", European Society of Endocrinology, 26 pages (2009).
Anaissie, J. et al., "Testosterone Replacement Therapy and Components of the Metabolic Syndrome", Sex Med Rev, 1-11, (2017).
Gonzalez, J. et al., "Testosterone Replacement and Cardiovascular Disease Risk: What Do Endocrinologists Need to Know?", Cardiovasc. Endocrinol., 4(3):100-107, (2015).
Zitzmann, M. et al., "Androgen Receptor Gene CAG Repeat Length and Body Mass Index Modulate the Safety of Long-Term Intramuscular Testosterone Undecanoate Therapy in Hypogonadal Men", J. of Clin. Endocrinology & Metabolism, 92(10):3844-3853, (2007).

* cited by examiner

*Primary Examiner* — San Ming R Hui
(74) *Attorney, Agent, or Firm* — Sheridan Ross P.C.

(57) ABSTRACT

Methods of treating a testosterone deficiency or its symptoms with a pharmaceutical formulation of testosterone esters are provided. In some embodiments, the subject has adequately controlled blood pressure.

27 Claims, No Drawings

METHODS OF TREATING TESTOSTERONE DEFICIENCY

Testosterone (T) is a primary androgenic hormone produced in the interstitial cells of the testes and is responsible for normal growth, development and maintenance of male sex organs and secondary sex characteristics (e.g., deepening voice, muscular development, facial hair, etc.). Throughout adult life, testosterone is necessary for proper functioning of the testes and its accessory structures, prostate and seminal vesicle; for sense of well-being; and for maintenance of libido, erectile potency.

Testosterone deficiency—insufficient secretion of T characterized by low total T concentrations—can give rise to medical conditions (e.g., hypogonadism) in males. Symptoms associated with male hypogonadism include impotence and decreased sexual desire, fatigue and loss of energy, mood depression, regression of secondary sexual characteristics, decreased muscle mass, and increased fat mass. Furthermore, hypogonadism in men is a risk factor for osteoporosis, metabolic syndrome, type II diabetes and cardiovascular disease.

Various testosterone replacement therapies are commercially available for the treatment of male hypogonadism. Pharmaceutical preparations include both testosterone and testosterone derivatives in the form of intramuscular injections, implants, oral tablets of alkylated T (e.g., methyltestosterone), topical gels, topical patches, or an intranasal gel.

Despite the advances that have been made in this field, there remains a need for new therapeutic products useful to treatment of testosterone deficiency. One such agent is testosterone undecanoate, which has the following chemical structure:

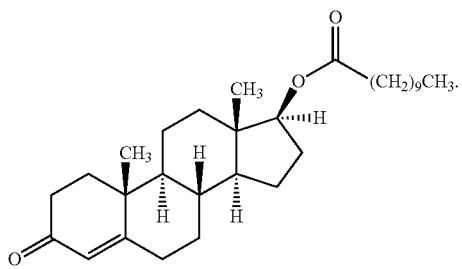

A formulation of testosterone undecanoate has been reported in the FDA approved drug label JATENZO®. The formulation also includes oleic acid, polyoxyl 40 hydrogenated castor oil (Cremophor RH 40), borage seed oil, peppermint oil, and butylated hydroxytoluene.

There is a significant, unmet need for methods for treating of testosterone deficiency. The present disclosure fulfills these and other needs, as evident in reference to the following disclosure.

SUMMARY

Provided is a method of treating conditions associated with a deficiency or absence of endogenous testosterone in a subject in need thereof who has adequately controlled blood pressure, the method comprising: administering daily to the subject a defined dose of an oral pharmaceutical composition comprising testosterone undecanoate in a carrier comprising at least one lipophilic surfactant and at least one hydrophilic surfactant.

These and other aspects of the invention will be apparent upon reference to the following detailed description. To this end, various references are set forth herein which describe in more detail certain background information, procedures, compounds, and/or compositions, and are each hereby incorporated by reference in their entirety.

DETAILED DESCRIPTION

Abbreviations and Definitions

To facilitate understanding of the invention, a number of terms and abbreviations as used herein are defined below as follows:

When introducing elements of the present invention or the particular embodiment(s) thereof, the articles "a", "an", "the" and "said" are intended to mean that there are one or more of the elements. The terms "comprising", "including" and "having" are intended to be inclusive and mean that there may be additional elements other than the listed elements.

The term "and/or" when used in a list of two or more items, means that any one of the listed items can be employed by itself or in combination with any one or more of the listed items. For example, the expression "A and/or B" is intended to mean either or both of A and B, i.e. A alone, B alone or A and B in combination. The expression "A, B and/or C" is intended to mean A alone, B alone, C alone, A and B in combination, A and C in combination, B and C in combination or A, B, and C in combination.

The term "hypertension" or "hypertensive" as used herein, refers to high blood pressure stage 1 and/or high blood pressure stage 2. High blood pressure stage 1 is characterized by a systolic blood pressure of between 130 and 139 mm Hg or a diastolic blood pressure of 80-90 mm Hg. High blood pressure stage 2 is characterized by a systolic blood pressure of 140 mm Hg or higher or a diastolic blood pressure of 90 mm Hg or higher.

The term "antihypertensive therapy" as used herein, refers to medications to treat high blood pressure, including without limitation:

diuretics, such as bumetanide, chlorothiazide, chlorthalidone, ethacrynate, furosemide, indapamide, hydrochlorothiazide (HCTZ), methyclothiazide, metolazone, or torsemide;

angiotensin-converting enzyme (ACE) inhibitors, such as benazepril hydrochloride, captopril, enalapril maleate, fosinopril sodium, lisinopril, moexipril, perindopril, quinapril hydrochloride, ramipril, or trandolapril;

angiotensin II receptor blockers, such as candesartan or losartan;

calcium channel blockers such as amlodipine, clevidipine, diltiazem, felodipine, isradipine, nicardipine, nifedipine, nimodipine, nisoldipine, or verapamil;

alpha blockers, such as doxazosin, terazosin or prazosin;

beta blockers, such as acebutolol, atenolol, bisoprolol fumarate, carvedilol, esmilol, labetalol, metoprolol tartrate and metoprolol succinate, nadolol, nebivolol, penbutolol sulfate, propranolol, sotalol, or bisoprolol;

aldosterone antagonists, such as spironolactone or eplerenone, epithelial Na-channel blockers, such as amiloride and triamterene, peripheral adrenergic inhibitors such as guanadrel, guanethidine monosulfate, or reserpine;

renin inhibitors, such as aliskiren;

vasodilators, such as hydralazine and minoxidil; and central-acting agents such as clonidine, guanfacine or methyldopa, and combinations thereof.

In some embodiments, antihypertensive therapy refers to valsartan, metoprolol, valsaran/HCTZ, olmesartan/HCTZ, lisinopril, amlodipine, or hydrochlorothiazide.

The term "about," as used herein, is intended to qualify the numerical values that it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

As used herein, "co-administer" and "co-administration" and variants thereof mean the administration of at least two drugs to a patient either subsequently, simultaneously, or consequently proximate in time to one another (e.g., within the same day, or week or period of 30 days, or sufficiently proximate that each of the at least two drugs can be simultaneously detected in the blood plasma). When co-administered, two or more active agents can be co-formulated as part of the same composition or administered as separate formulations. This also may be referred to herein as "concomitant" administration or variants thereof.

As used herein, "adjusting administration", "altering administration", "adjusting dosing", or "altering dosing" are all equivalent and mean tapering off, reducing or increasing the dose of the substance, ceasing to administer the substance to the patient, or substituting a different active agent for the substance.

As used herein, "administering to a patient" refers to the process of introducing a composition or dosage form into the patient via an art-recognized means of introduction.

As used herein, "effective amount" and "therapeutically effective amount" of an agent, compound, drug, composition or combination is an amount which is nontoxic and effective for producing some desired therapeutic effect upon administration to a subject or patient (e.g., a human subject or patient). The precise therapeutically effective amount for a subject may depend upon, e.g., the subject's size and health, the nature and extent of the condition, the therapeutics or combination of therapeutics selected for administration, and other variables known to those of skill in the art. The effective amount for a given situation is determined by routine experimentation and is within the judgment of the clinician.

As used herein, "informing" means referring to or providing published material, for example, providing an active agent with published material to a user; or presenting information orally, for example, by presentation at a seminar, conference, or other educational presentation, by conversation between a pharmaceutical sales representative and a medical care worker, or by conversation between a medical care worker and a patient; or demonstrating the intended information to a user for the purpose of comprehension.

As used herein, "labeling" means all labels or other means of written, printed, graphic, electronic, verbal, or demonstrative communication that is upon a pharmaceutical product or a dosage form or accompanying such pharmaceutical product or dosage form.

As used herein, "a "medical care worker" means a worker in the health care field who may need or utilize information regarding an active agent, including a dosage form thereof, including information on safety, efficacy, dosing, administration, or pharmacokinetics. Examples of medical care workers include physicians, pharmacists, physician's assistants, nurses, aides, caretakers (which can include family members or guardians), emergency medical workers, and veterinarians.

As used herein, "Medication Guide" means an FDA-approved patient labeling for a pharmaceutical product conforming to the specifications set forth in 21 CFR 208 and other applicable regulations which contains information for patients on how to safely use a pharmaceutical product. A medication guide is scientifically accurate and is based on, and does not conflict with, the approved professional labeling for the pharmaceutical product under 21 CFR 201.57, but the language need not be identical to the sections of approved labeling to which it corresponds. A medication guide is typically available for a pharmaceutical product with special risk management information.

As used herein, "patient" or "individual" or "subject" means a mammal, including a human, for whom or which therapy is desired, and generally refers to the recipient of the therapy.

As used herein, "patient package insert" means information for patients on how to safely use a pharmaceutical product that is part of the FDA-approved labeling. It is an extension of the professional labeling for a pharmaceutical product that may be distributed to a patient when the product is dispensed which provides consumer-oriented information about the product in lay language, for example it may describe benefits, risks, how to recognize risks, dosage, or administration.

As used herein, "pharmaceutically acceptable" refers to a material that is not biologically or otherwise undesirable, i.e., the material may be incorporated into a pharmaceutical composition administered to a patient without causing any undesirable biological effects or interacting in a deleterious manner with any of the other components of the composition in which it is contained. When the term "pharmaceutically acceptable" is used to refer to a pharmaceutical carrier or excipient, it is implied that the carrier or excipient has met the required standards of toxicological and manufacturing testing or that it is included on the Inactive Ingredient Guide prepared by the U.S. Food and Drug administration. "Pharmacologically active" (or simply "active") as in a "pharmacologically active" (or "active") derivative or analog, refers to a derivative or analog having the same type of pharmacological activity as the parent compound and approximately equivalent in degree. The term "pharmaceutically acceptable salts" include acid addition salts which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

As used herein, a "product" or "pharmaceutical product" means a dosage form of an active agent plus published material, and optionally packaging.

As used herein, "product insert" means the professional labeling (prescribing information) for a pharmaceutical product, a patient package insert for the pharmaceutical product, or a medication guide for the pharmaceutical product.

As used herein, "professional labeling" or "prescribing information" means the official description of a pharmaceutical product approved by a regulatory agency (e.g., FDA or EMEA) regulating marketing of the pharmaceutical product, which includes a summary of the essential scientific information needed for the safe and effective use of the drug, such as, for example indication and usage; dosage and administration; who should take it; adverse events (side effects); instructions for use in special populations (pregnant women, children, geriatric, etc.); safety information for the patient, and the like.

As used herein, "published material" means a medium providing information, including printed, audio, visual, or electronic medium, for example a flyer, an advertisement, a product insert, printed labeling, an internet web site, an internet web page, an internet pop-up window, a radio or television broadcast, a compact disk, a DVD, an audio recording, or other recording or electronic medium.

As used herein, "risk" means the probability or chance of adverse reaction, injury, or other undesirable outcome arising from a medical treatment. An "acceptable risk" means a measure of the risk of harm, injury, or disease arising from a medical treatment that will be tolerated by an individual or group. Whether a risk is "acceptable" will depend upon the advantages that the individual or group perceives to be obtainable in return for taking the risk, whether they accept whatever scientific and other advice is offered about the magnitude of the risk, and numerous other factors, both political and social. An "acceptable risk" of an adverse reaction means that an individual or a group in society is willing to take or be subjected to the risk that the adverse reaction might occur since the adverse reaction is one whose probability of occurrence is small, or whose consequences are so slight, or the benefits (perceived or real) of the active agent are so great. An "unacceptable risk" of an adverse reaction means that an individual or a group in society is unwilling to take or be subjected to the risk that the adverse reaction might occur upon weighing the probability of occurrence of the adverse reaction, the consequences of the adverse reaction, and the benefits (perceived or real) of the active agent. "At risk" means in a state or condition marked by a high level of risk or susceptibility. Risk assessment consists of identifying and characterizing the nature, frequency, and severity of the risks associated with the use of a product.

As used herein, "safety" means the incidence or severity of adverse events associated with administration of an active agent, including adverse effects associated with patient-related factors (e.g., age, gender, ethnicity, race, target illness, abnormalities of renal or hepatic function, co-morbid illnesses, genetic characteristics such as metabolic status, or environment) and active agent-related factors (e.g., dose, plasma level, duration of exposure, or concomitant medication).

As used herein, "treating" or "treatment" refers to therapeutic applications to slow or stop progression of a disorder, prophylactic application to prevent development of a disorder, and/or reversal of a disorder. Reversal of a disorder differs from a therapeutic application which slows or stops a disorder in that with a method of reversing, not only is progression of a disorder completely stopped, cellular behavior is moved to some degree, toward a normal state that would be observed in the absence of the disorder.

The term "plasma," as used herein, is intended to mean the liquid component of blood that holds the blood cells in whole blood in suspension; this makes plasma the extracellular matrix of blood cells. It makes up about 55% of the body's total blood volume. It is mostly water (up to 95% by volume), and contains dissolved proteins (6-8%) (i.e.—serum albumins, globulins, and fibrinogen), glucose, clotting factors, electrolytes ($Na^+$, $Ca^{2+}$, $Mg^{2+}$, $HCO_3^-$, $Cl^-$, etc.), hormones, carbon dioxide (plasma being the main medium for excretory product transportation) and oxygen. This is in contrast to blood serum which is blood plasma without clotting factors. Further, plasma is derived from blood that is collected differently than when serum is collected, by allowing the blood to clot prior to centrifugation when collecting serum versus immediate centrifugation when collecting plasma.

Methods

Provided is a method of treating conditions associated with a deficiency or absence of endogenous testosterone in a subject in need thereof who has adequately controlled blood pressure, the method comprising: administering daily to the subject a defined dose of an oral pharmaceutical composition comprising testosterone undecanoate in a carrier comprising at least one lipophilic surfactant and at least one hydrophilic surfactant.

Also provided is a method of treating conditions associated with a deficiency or absence of endogenous testosterone in a subject in need thereof, the method comprising: assessing the subject's blood pressure; and if the subject's blood pressure is adequately controlled, administering daily to the subject a defined dose of an oral pharmaceutical composition comprising testosterone undecanoate in a carrier comprising at least one lipophilic surfactant and at least one hydrophilic surfactant.

Also provided is a method of treating conditions associated with a deficiency or absence of endogenous testosterone in a subject in need thereof, the method comprising: determining if the subject has been diagnosed as having hypertension; determining whether the subject's blood pressure is adequately controlled; and if the subject's blood pressure is adequately controlled, administering daily to the subject a defined dose of an oral pharmaceutical composition comprising testosterone undecanoate in a carrier comprising at least one lipophilic surfactant and at least one hydrophilic surfactant.

Also provided is a method of treating conditions associated with a deficiency or absence of endogenous testosterone in a subject in need thereof who does not have adequately controlled blood pressure, the method comprising: administering antihypertensive therapy to the subject in an amount and for a duration such that the subject's blood pressure is adequately controlled and administering daily to the subject a defined dose of an oral pharmaceutical composition comprising testosterone undecanoate in a carrier comprising at least one lipophilic surfactant and at least one hydrophilic surfactant.

In some embodiments, the oral pharmaceutical composition is administered twice daily (BID). In some embodiments, the oral pharmaceutical composition is administered three times daily (TID). In some embodiments, the oral pharmaceutical composition is administered once daily (QD).

In some embodiments, the method further comprises:
administering daily for a first period of time to the subject the defined dose of the oral pharmaceutical composition;
monitoring the subject for new-onset hypertension or exacerbation of pre-existing hypertension; and
treating the subject for new-onset hypertension or exacerbation of pre-existing hypertension.

In some embodiments, the first period of time is approximately three weeks.

In some embodiments, the method further comprises:
administering daily to the subject an increased dose of the oral pharmaceutical composition;
monitoring the subject for new-onset hypertension or exacerbation of pre-existing hypertension; and treating the subject for new-onset hypertension or exacerbation of pre-existing hypertension.

In some embodiments, the method further comprises: informing the subject that administration of the oral pharmaceutical composition may result in an increase in blood pressure. In some embodiments, administration of the oral pharmaceutical composition results in an average increase of systolic blood pressure of 4.9 mm Hg based on ambulatory blood pressure monitoring. In some embodiments, administration of the oral pharmaceutical composition results in an average increase of systolic blood pressure of 2.8 mm Hg based on blood pressure cuff measurements.

In some embodiments, the method further comprises: informing the subject that co-administration of the oral pharmaceutical composition with a prescription medication known to increase blood pressure and/or a nonprescription analgesic and/or a cold medication may result in additional increases in blood pressure.

In some embodiments, the method further comprises: monitoring the subject's blood pressure.

In some embodiments, the method further comprises: informing the subject that administration of the oral pharmaceutical composition may result in an increased risk of a major adverse cardiovascular event (MACE). In some embodiments, the MACE is chosen from myocardial infarction, stroke and cardiovascular death. In some embodiments, the subject has one or more cardiovascular risk factors or established cardiovascular disease.

In some embodiments, the subject is being co-administered a prescription medication known to increase blood pressure and/or a nonprescription analgesic and/or a cold medication may result in additional increases in blood pressure.

In some embodiments, the subject is not being administered a prescription medication known to increase blood pressure and/or a nonprescription analgesic and/or a cold medication may result in additional increases in blood pressure.

In some embodiments, the subject is not being treated with antihypertensive therapy.

In some embodiments, the subject is being treated with antihypertensive therapy.

In some embodiments, the subject does not have a history of hypertension.

In some embodiments, the subject has a history of hypertension.

In some embodiments, the subject is diagnosed with hypogonadal conditions associated with structural or genetic etiologies.

In some embodiments, the subject is diagnosed with primary hypogonadism. In some embodiments, the subject is diagnosed with testicular failure due to cryptorchidism, bilateral torsion, orchitis, vanishing testis syndrome, orchiectomy, Klinefelter syndrome, chemotherapy, or toxic damage from alcohol or heavy metals.

In some embodiments, the subject is diagnosed with hypogonadotropic hypogonadism. In some embodiments, the subject is diagnosed with gonadotropin or luteinizing hormone-releasing hormone (LHRH) deficiency or pituitary-hypothalamic injury from tumors, trauma, or radiation.

In some embodiments, the subject is not diagnosed with age-related hypogonadism.

In some embodiments, the method further comprises: collecting the subject's blood sample;
measuring the serum testosterone concentration in the subject; and if the measured serum testosterone concentration is less than about 425 ng/dL, increasing the dose of testosterone undecanoate administered;
if the measured serum testosterone concentration is greater than about 970 ng/dL decreasing the dose of testosterone undecanoate; and
if the measured serum testosterone concentration is between about 425 ng/dL and about 970 ng/dL, maintaining the dose of testosterone undecanoate administered.

In some embodiments, these steps are repeated until the serum testosterone concentration from blood collected 6 hours post-dose in the subject is between about 425 and about 970 ng/dL.

In some embodiments, the defined dose of testosterone undecanoate in the oral pharmaceutical composition is equivalent to about 150 mg of testosterone. In some embodiments, the oral pharmaceutical composition administered comprises about 237 mg of testosterone undecanoate that equates to 150 mg of testosterone.

In some embodiments, the defined dose of testosterone undecanoate in the oral pharmaceutical composition is equivalent to about 200 mg of testosterone per dose. In some embodiments, the oral pharmaceutical composition administered comprises about 316 mg of testosterone undecanoate that equates to 200 mg testosterone per dose.

In some embodiments, the defined dose of testosterone undecanoate in the oral pharmaceutical composition is equivalent to about 250 mg of testosterone per dose. In some embodiments, the oral pharmaceutical composition administered comprises about 396 mg of testosterone undecanoate that equates to 250 mg testosterone per dose.

In some embodiments, the defined dose of testosterone undecanoate in the oral pharmaceutical composition is equivalent to about 125 mg of testosterone per dose. In some embodiments, the oral pharmaceutical composition administered comprises about 198 mg of testosterone undecanoate that equates to 125 mg testosterone per dose.

In some embodiments, the defined dose of testosterone undecanoate in the oral pharmaceutical composition is equivalent to about 100 mg of testosterone per dose. In some embodiments, the oral pharmaceutical composition administered comprises about 158 mg of testosterone undecanoate that equates to 100 mg testosterone per dose.

In some embodiments, the dose of testosterone undecanoate in the administered oral pharmaceutical composition is increased by the equivalent of about 25 to about 75 mg of testosterone when the serum testosterone 6 hours after the dose (i.e., $C_6$) in the subject is less than about 425 ng/dL, and decreased by the equivalent of about 10 to about 75 mg of testosterone when the serum testosterone $C_6$ in the subject is greater than about 970 ng/dL.

In some embodiments, the dose of testosterone undecanoate is increased by about 40 mg to about 80 mg when the measured serum testosterone concentration in the subject is less than about 425 ng/dL.

In some embodiments, the dose of testosterone undecanoate is increased by the equivalent of about 40 to about 60 mg of testosterone when the serum testosterone $C_6$ in the subject is less than about 425 ng/dL. In some embodiments, the dose of testosterone undecanoate is increased by the equivalent of about 50 mg of testosterone when the serum testosterone $C_6$ in the subject is less than about 425 ng/dL.

In some embodiments, the dose of testosterone undecanoate is decreased by about 10 mg to about 40 mg when the measured serum testosterone concentration in the subject is greater than about 970 ng/dL.

In some embodiments, the dose of testosterone undecanoate is decreased by the equivalent of about 10 to about 60 mg of testosterone when the serum testosterone $C_6$ in the subject is greater than about 970 ng/dL. In some embodiments, the dose of testosterone undecanoate is decreased by the equivalent of about 25 to about 50 mg of testosterone when the serum testosterone $C_6$ in the subject is greater than about 970 ng/dL. In some embodiments, the dose of testosterone undecanoate is decreased by the equivalent of about 25 mg of testosterone when the serum testosterone $C_6$ in the subject is greater than about 970 ng/dL.

In some embodiments, the 237 mg dose of TU is increased to a 316 mg dose of TU when the subject's measured serum testosterone concentration is less than about 425 ng/dL or decreased to a dose of 198 mg of TU when the subject's measured serum testosterone concentration is greater than about 970 ng/dL.

In some embodiments, the 316 mg dose of TU is increased to a dose of 396 mg of TU when the subject's measured serum testosterone concentration is less than about 425 ng/dL or decreased to a dose of 237 mg of TU when the subject's measured serum testosterone concentration is greater than about 970 ng/dL.

In some embodiments, the 198 mg dose of TU is increased to a dose of 237 mg of TU when the subject's measured serum testosterone concentration is less than about 425 ng/dL or decreased to a dose of 158 mg of TU when the subject's measured serum testosterone concentration is greater than about 970 ng/dL.

In some embodiments, the 396 mg dose of TU is decreased to a dose of 316 mg of TU when the subject's measured serum testosterone concentration is greater than about 970 ng/dL.

In some embodiments, the 158 mg dose of TU is increased to a dose of 198 mg of TU when the subject's measured serum testosterone concentration is less than about 425 ng/dL or treatment is discontinued when the subject's measured serum testosterone concentration is greater than about 970 ng/dL.

In some embodiments, the dose adjustment scheme is as shown in Table 1.

TABLE 1

| Testosterone Concentration in Serum From Plain (Red-Top) Tube Drawn 6 hours After Dose | Current Dose (mg, BID) | New Dose (mg, BID) |
|---|---|---|
| <425 ng/dL | 158 | 198 |
|  | 198 | 237 |
|  | 237 | 316 |
|  | 316 | 398 |
| 425-970 ng/dL | No Dose Change | |
| >970 ng/dL | 396 | 316 |
|  | 316 | 237 |
|  | 237 | 198 |
|  | 198 | 158 |
|  | 158 | Discontinue Treatment |

In some embodiments, the blood is drawn at least 7 days after starting treatment and following dose adjustment.

In some embodiments, the blood is drawn 4-8 hours (i.e., $C_{4-8}$) after the administration of the dose. In some embodiments, the blood is drawn 5-7 hours after the administration of the dose. In some embodiments, the blood is drawn 6 hours after the administration of the dose (i.e., $C_6$).

In some embodiments, the circulating testosterone concentration is measured in serum. In some embodiments, the serum testosterone level at 6 hours after administration ($C_6$) is a suitable approximation of $C_{avg}$. In some embodiments, the serum testosterone concentration is measured five to seven hours after administering the oral pharmaceutical composition. In some embodiments, the serum testosterone concentration at 6 hours after administration of the morning dose is used to approximate $C_{avg}$.

In some embodiments, the serum testosterone $C_{avg}$ is estimated on the basis of a single blood sample (i.e., $C_6$ serum T concentration). In some embodiments, the serum testosterone $C_{avg}$ is estimated on the basis of a single blood sample collected 4 to 8 hours after administering the oral pharmaceutical composition. In some embodiments, the serum testosterone $C_{avg}$ is estimated on the basis of a single blood sample collected 5 to 7 hours after administering the oral pharmaceutical composition. In some embodiments, the serum testosterone $C_{avg}$ is estimated on the basis of a single blood sample collected 6 hours after administering the oral pharmaceutical composition.

In some embodiments, the steady-state serum testosterone $C_{avg}$ is estimated based on the measurement of T in a single blood sample collected about 4 to 8 hours after oral T dose after at least seven days of daily treatment with the oral pharmaceutical composition. In some embodiments, the steady-state serum testosterone $C_{avg}$ is estimated based on the measurement of T in a single blood sample collected about 5 to 7 hours after oral T dose after at least seven days of daily treatment with the oral pharmaceutical composition. In some embodiments, the steady-state serum testosterone $C_{avg}$ is estimated based on the measurement of T in a single blood sample collected about 6 hours after oral T dose after at least seven days of daily treatment with the oral pharmaceutical composition.

In some embodiments, the average serum testosterone concentration (i.e., $C_{avg}$) is determined based on the measurement of T via an immunometric assay, or a liquid chromatography tandem mass spectrometry (LC-MS/MS) assay.

In some embodiments, measuring the subject's testosterone concentration comprises estimating the subject's blood testosterone concentration by measuring the subject's serum testosterone concentration and dividing that concentration by a conversion factor. In some embodiments, the conversion factor is between about 1.0 and about 1.4. In some embodiments, the conversion factor is between about 1.032 and about 1.396. In some embodiments, the conversion factor is 1.214. In some embodiments, if the sample is a serum sample, then dividing the T concentration measured in serum by 1.214 would yield the expected T concentration in NaF-EDTA plasma.

In some embodiments, the serum testosterone $C_{avg}$ is determined after at least 10 to 14 days of daily treatment with the oral pharmaceutical composition. In some embodiments, the serum testosterone $C_{avg}$ is determined after at least 30 days of daily treatment with the oral pharmaceutical composition. In some embodiments, the dose of oral pharmaceutical composition is titrated after 21 days of daily treatment.

In some embodiments, the dose of oral pharmaceutical composition is titrated after 56 days of daily treatment. In some embodiments, the dose of oral pharmaceutical composition is titrated after 105 days of daily treatment. In some embodiments, the dose of oral pharmaceutical composition is titrated after at least 30 days of daily treatment. In some embodiments, the dose of oral pharmaceutical composition is titrated after 35 days of daily treatment. In some embodiments, the dose of oral pharmaceutical composition is titrated after at least 60 days of daily treatment. In some embodiments, the dose of oral pharmaceutical composition is titrated after 70 days of daily treatment.

In some embodiments, the oral pharmaceutical composition is administered in close proximity to a meal (e.g., immediately prior or after a meal, or 15 minutes prior to after a meal or 30 minutes prior to or after a meal) wherein the meal contains at least about 15 g of fat. In some embodiments, the meal contains at least about 30 g of fat. In some embodiments, the meal contains at least about 45 g of fat.

In some embodiments, the oral pharmaceutical composition comprises a testosterone undecanoate solubilized in a carrier comprising at least one lipophilic surfactant and at least one hydrophilic surfactant in a total lipophilic surfactant to total hydrophilic surfactant ratio (w/w) falling in the range of about 6:1 to 3.5:1, which composition, upon once- or twice-daily oral administration, provides an average serum testosterone concentration at steady state falling in the range of about 425 to about 970 ng/dL.

In some embodiments, the composition comprises 15-30% (w/w) of the testosterone undecanoate. In some embodiments, the composition comprises 15-20% (w/w) of the testosterone undecanoate. In some embodiments, the composition comprises 18-22% (w/w) of the testosterone undecanoate. In some embodiments, the composition comprises 25-30% (w/w) of the testosterone undecanoate.

In some embodiments, the oral pharmaceutical composition comprises about 10-20 percent by weight of solubilized testosterone undecanoate, about 5-20 percent by weight of hydrophilic surfactant, about 50-70 percent by weight of lipophilic surfactant; and about 10-15 percent by weight of digestible oil, wherein the oral pharmaceutical composition is free of ethanol.

In some embodiments, the oral pharmaceutical composition comprises: about 15-20 percent by weight of solubilized testosterone undecanoate, about 5-20 percent by weight of hydrophilic surfactant, about 50-70 percent by weight of lipophilic surfactant; and about 10-15 percent by weight of digestible oil.

In some embodiments, the oral pharmaceutical composition comprises: about 15-20 percent by weight of solubilized testosterone undecanoate, about 5-20 percent by weight of hydrophilic surfactant, about 50-70 percent by weight of lipophilic surfactant; and about 1-10 percent by weight of polyethylene glycol 8000.

In some embodiments, the hydrophilic surfactant exhibits an HLB of 10 to 45. In some embodiments, the hydrophilic surfactant exhibits an HLB of 10 to 15.

In some embodiments, the hydrophilic surfactant is selected from the group consisting of polyoxyethylene sorbitan fatty acid esters, hydrogenated castor oil ethoxylates, polyethylene glycol mono- and di-glycerol esters of caprylic, capric, palmitic and stearic acids, fatty acid ethoxylates, polyethylene glycol esters of alpha-tocopherol and its esters and combinations thereof. In some embodiments, the hydrophilic surfactant is a hydrogenated castor oil ethoxylate. In some embodiments, the hydrophilic surfactant is Cremophor RH 40 (polyoxyethyleneglycerol trihydroxystearate).

In some embodiments, the lipophilic surfactant exhibits an HLB of less than 10. In some embodiments, the lipophilic surfactant exhibits an HLB of less than 5. In some embodiments, the lipophilic surfactant exhibits an HLB of 1 to 2.

In some embodiments, the lipophilic surfactant is a fatty acid selected from the group consisting of octanoic acid, decanoic acid, undecanoic acid, lauric acid, myristic acid, palmitic acid, pamitoleic acid, stearic acid, oleic acid, linoleic acid, alpha- and gamma linolenic acid, arachidonic acid, and combinations thereof.

In some embodiments, the lipophilic surfactant is chosen from mono- and/or di-glycerides of fatty acids, such as glyceryl distearate, Imwitor 988 (glyceryl mono-/di-caprylate), Imwitor 742 (glyceryl mono-di-caprylate/caprate), Imwitor 308 (glyceryl mono-caprylate), Imwitor 191 (glyceryl mono-stearate), Softigen 701 (glyceryl mono-/di-ricinoleate), Capmul MCM (glyceryl caprylate/caprate), Capmul MCM(L) (liquid form of Capmul MCM), Capmul GMO (glyceryl mono-oleate), Capmul GDL (glyceryl dilaurate), Maisine (glyceryl mono-linoleate), Peceol (glyceryl mono-oleate), Myverol 18-92 (distilled monoglycerides from sunflower oil) and Myverol 18-06 (distilled monoglycerides from hydrogenated soyabean oil), Precirol ATO 5 (glyceryl palmitostearate) and Gelucire 39/01 (semi-synthetic glycerides, i.e., $C_{12-18}$ mono-, di- and tri-glycerides), and combinations thereof.

In some embodiments, the lipophilic surfactant is chosen from acetic, succinic, lactic, citric and/or tartaric esters of mono- and/or di-glycerides of fatty acids, for example, Myvacet 9-45 (distilled acetylated monoglycerides), Miglyol 829 (caprylic/capric diglyceryl succinate), Myverol SMG (mono/di-succinylated monoglycerides), Imwitor 370 (glyceryl stearate citrate), Imwitor 375 (glyceryl monostearate/citrate/lactate) and Crodatem T22 (diacetyl tartaric esters of monoglycerides); Propylene glycol mono- and/or di-esters of fatty acids, for example, Lauroglycol (propylene glycol monolaurate), Mirpyl (propylene glycol monomyristate), Captex 200 (propylene glycol dicaprylate/dicaprate), Miglyol 840 (propylene glycol dicaprylate/dicaprate) and Neobee M-20 (propylene glycol dicaprylate/dicaprate); Polyglycerol esters of fatty acids such as Plurol oleique (polyglyceryl oleate), Caprol ET (polyglyceryl mixed fatty acids) and Drewpol 10.10.10 (polyglyceryl oleate); Castor oil ethoxylates of low ethoxylate content (HLB<10) such as Etocas 5 (5 moles of ethylene oxide reacted with 1 mole of castor oil) and Sandoxylate 5 (5 moles of ethylene oxide reacted with 1 mole of castor oil; Acid and ester ethoxylates formed by reacting ethylene oxide with fatty acids or glycerol esters of fatty acids (HLB<10) such as Crodet 04 (polyoxyethylene (4) lauric acid), Cithrol 2MS (polyoxyethylene (2) stearic acid), Marlosol 183 (polyoxyethylene (3) stearic acid) and Marlowet G12DO (glyceryl 12 EO dioleate). Sorbitan esters of fatty acids, for example, Span 20 (sorbitan monolaurate), Crill 1 (sorbitan monolaurate) and Crill 4 (sorbitan mono-oleate); Transesterification products of natural or hydrogenated vegetable oil triglyceride and a polyalkylene polyol (HLB<10), e.g. Labrafil M1944CS (polyoxyethylated apricot kernel oil), Labrafil M2125CS (polyoxyethylated corn oil) and Gelucire 37/06 (polyoxyethylated hydrogenated coconut); Alcohol ethyoxylates (HLB<10), e.g. Volpo N3 (polyoxyethylated (3) oleyl ether), Brij 93 (polyoxyethylated (2) oleyl ether), Marlowet LA4 (polyoxyethylated (4) lauryl ether); and Pluronics, for example, Polyoxyethylene-polyoxypropylene co-polymers and block co-polymers (HLB<10) e.g. Synperonic PE L42 (HLB=8) and Synperonic PE L61 (HLB=3)

In some embodiments, the lipophilic surfactant is glyceryl monolinoleate.

In some embodiments, the oral pharmaceutical composition further includes digestible oil. A digestible oil is defined herein as an oil that is capable of undergoing de-esterification or hydrolysis in the presence of pancreatic lipase in vivo under normal physiological conditions. In some embodiments, the digestible oil is a vegetable oil selected from the group consisting of soybean oil, safflower seed oil, corn oil, olive oil, castor oil, cottonseed oil, arachis oil, sunflower seed oil, coconut oil, palm oil, rapeseed oil, black currant oil, evening primrose oil, grape seed oil, wheat germ oil, sesame oil, avocado oil, almond oil, borage oil, peppermint oil and apricot kernel oil. Specifically, digestible oils may be complete glycerol triesters of medium chain ($C_7$-$C_{13}$) or long chain ($C_{14}$-$C_{22}$) fatty acids with low molecular weight (up to $C_6$) mono-, di- or polyhydric alcohols. Some examples of digestible oils for use the oral pharmaceutical composition include: vegetable oils (e.g., soybean oil, safflower seed oil, corn oil, olive oil, castor oil, cottonseed oil, arachis oil, sunflower seed oil, coconut oil, palm oil, rapeseed oil, black currant oil, evening primrose oil, grape seed oil, wheat germ oil, sesame oil, avocado oil, almond, borage, peppermint and apricot kernel oils) and animal oils (e.g., fish liver oil, shark oil and mink oil). In some embodiments, the digestible oil is a vegetable oil. In some embodiments, the vegetable oil is soybean oil, safflower seed oil, corn oil, olive oil, castor oil, cottonseed oil, arachis oil, sunflower seed oil, coconut oil, palm oil, rapeseed oil, evening primrose oil, grape seed oil, wheat germ oil, sesame oil, avocado oil, almond oil, borage oil, peppermint oil, apricot kernel oil, or combinations thereof. Particular digestible oils are those with high gamma-linolenic acid (GLA) content such as, black currant oil, primrose oil and borage oil, as well as any other digestible oil that can be enriched in GLA acid through enzymatic processes.

In some embodiments, the oral pharmaceutical composition is filled into a hard or soft gelatin capsule.

In some embodiments, the oral pharmaceutical composition is a liquid, semi-solid or solid dosage form. In some embodiments, the oral pharmaceutical compositions administered in the present invention are liquid or semi-solid at ambient temperatures. Furthermore, these pharmaceutical compositions can be transformed into solid dosage forms through adsorption onto solid carrier particles, such as silicon dioxide, calcium silicate or magnesium aluminometasilicate to obtain free-flowing powders that can be either filled into hard capsules or compressed into tablets. Hence, the term "solubilized" herein, should be interpreted to describe an active pharmaceutical ingredient (API), which is dissolved in a liquid solution or which is uniformly dispersed in a solid carrier. In addition, sachet type dosage forms can be formed and used. In some embodiments, the oral pharmaceutical composition is filled into a hard or soft gelatin capsule.

In some embodiments, the oral pharmaceutical composition exhibits a percent (%) in vitro dissolution profile in 5% Triton X-100 solution in phosphate buffer, pH 6.8, indicating release from the composition of substantially all of the solubilized testosterone undecanoate within about 2 hours.

In some embodiments, the oral pharmaceutical composition exhibits a percent (%) in vitro dissolution profile in 5% Triton X-100 solution in phosphate buffer, pH 6.8, indicating release from the composition of substantially all of the solubilized testosterone undecanoate within about 1 hour.

In some embodiments, the composition is free of monohydric alcohol. In some embodiments, the monohydric alcohol is chosen from $C_2$-$C_{18}$ aliphatic or aromatic alcohol. In some embodiments, the monohydric alcohol is chosen from ethanol and benzyl alcohol.

Optional cosolvents suitable with the oral pharmaceutical composition are, for example, water, short chain mono-, di-, and polyhydric alcohols, such as ethanol, benzyl alcohol, glycerol, propylene glycol, propylene carbonate, polyethylene glycol (PEG) with an average molecular weight of about 200 to about 10,000, diethylene glycol monoethyl ether (e.g., Transcutol HP), and combinations thereof. In some embodiments, the compositions contain between 0% and 10% (w/w) of polyethylene glycol with an average molecular weight of about 8,000 (PEG-8000). In some embodiments, the compositions contain between 5% and 10% (w/w) of PEG-8000.

In some embodiments, the oral pharmaceutical composition comprises at least one hydrophilic surfactant comprises Cremophor RH 40 (polyoxyethyleneglycerol trihydroxystearate).

In some embodiments, the lipophilic surfactant comprises oleic acid.

In some embodiments, the oral pharmaceutical composition comprises about 18 to 22 percent by weight of a solubilized testosterone undecanoate.

In some embodiments, the testosterone undecanoate is solubilized in a carrier substantially free of ethanol.

In some embodiments, the oral pharmaceutical composition comprises 15 to 17 percent by weight of the at least one hydrophilic surfactant.

In some embodiments, the oral pharmaceutical composition comprises 50 to 55 percent by weight of the at least one lipophilic surfactant.

In some embodiments, the oral pharmaceutical composition comprises about 19.8 percent by weight of solubilized testosterone undecanoate, about 51.6 percent by weight of oleic acid, about 16.1 percent by weight of polyoxyethylene (40) hydrogenated castor oil, about 10 percent by weight of borage seed oil, about 2.5 percent by weight of peppermint oil, and about 0.03 percent by weight of butylated hydroxytoluene (BHT).

Particular formulations of TU filled into size "00" capsules in accordance with the present invention are:

Formulation A

| Ingredients | mg/capsule | %, w/w |
| --- | --- | --- |
| Testosterone Undecanoate | 158.3 | 19.8 |
| Oleic Acid | 413.1 | 51.6 |
| Cremophor RH 40 | 128.4 | 16.1 |
| Borage Seed Oil | 80.0 | 10 |
| Peppermint Oil | 20.0 | 2.5 |
| BHT | 0.2 | 0.03 |
| Total | 800 | 100.03 |

Formulation B

| Ingredients | mg/capsule | %, w/w |
| --- | --- | --- |
| Testosterone Undecanoate | 158.3 | 19.8 |
| Oleic Acid | 412.5 | 51.6 |
| Cremophor RH 40 | 128.4 | 16.0 |
| Peppermint Oil | 20.0 | 2.5 |
| Borage Seed Oil + 0.03% BHT | 80.0 | 10 |
| Ascorbyl Palmitate | 0.8 | 0.1 |
| Total | 800 | 100 |

Formulation C

| Ingredients | mg/capsule | %, w/w |
| --- | --- | --- |
| Testosterone Undecanoate | 120 | 15 |
| Cremophor RH 40 | 128 | 16 |

-continued

| Ingredients | mg/capsule | %, w/w |
|---|---|---|
| Maisine 35-1 | 504 | 63 |
| Polyethylene Glycol 8000 | 48 | 6 |
| TOTAL | 800 | 100 |

In some embodiments, each morning and evening dose initially comprises about 237 mg of testosterone undecanoate.

In some embodiments, the oral pharmaceutical composition comprises about 15 percent by weight of testosterone undecanoate, about 63 percent by weight of glyceryl monolinoleate, about 16 percent by weight of polyoxyethylene (40) hydrogenated castor oil, and about 6 percent by weight of polyethylene glycol having a molecular weight of about 8000 g/mol (PEG 8000).

In some embodiments, the oral pharmaceutical composition comprises one or more additional therapeutic agents. In some embodiments, the additional therapeutic agents are selected from the group consisting of a synthetic progestin, an inhibitor of type-I and/or type II 5α-reductase (e.g., finasteride and dutasteride), an inhibitor of CYP3A4, thiazide diuretics, and calcium channel blockers, and combinations thereof. In some embodiments, the one or more additional therapeutic agents comprises a second testosterone ester. In some embodiments, the agent is borage oil. In some embodiments, the agent is peppermint oil and related substances such as menthol and menthol esters.

In some embodiments, the oral pharmaceutical composition comprises one or more additional component(s) that may biochemically modulate (1) testosterone ester absorption, (2) testosterone ester metabolism to testosterone, and/or (3) metabolism of testosterone to dihydrotestosterone (DHT). For example, the inclusion of medium to long chain fatty acid esters can enhance testosterone ester absorption. In this way, more testosterone ester may stave off hydrolysis in the gut and enter the blood stream. In other words, the fatty acid ester may competitively inhibit esterases that would otherwise metabolize the testosterone ester. Examples of other esters or combinations thereof include botanical extracts or benign esters used as food additives (e.g., propylparaben, octylacetate and ethylacetate).

Other components that can modulate testosterone ester absorption include "natural" and synthetic inhibitors of 5α-reductase, which is an enzyme present in enterocytes and other tissues that catalyzes the conversion of T to DHT. Complete or partial inhibition of this conversion may both increase and sustain increased plasma levels of T after oral dosing with testosterone ester while concomitantly reducing plasma DHT levels. Borage oil, which contains a significant amount of the 5α-reductase inhibitor, gamma-linolenic acid (GLA), is an example of a "natural" modulator of testosterone ester metabolism. Other than within borage oil, of course, GLA could be added directly as a separate component of a testosterone ester formulation of the invention. Furthermore, any digestible oil as listed above can be enzymatically enriched in GLA. Many natural inhibitors of 5α-reductase are known in the art (e.g., epigallocatechin gallate, a catechin derived primarily from green tea and saw palmetto extract from berries of the Serenoa repens species, phytosterols and lycopene), all of which may be suitable in the present invention. Non-limiting examples of synthetic 5α-reductase inhibitors suitable for use in the present invention include compounds such as finasteride, dutasteride and the like.

EXAMPLES

Example 1

Increase in Blood Pressure

In a 4-month clinical study, 24-hour ambulatory blood pressure monitoring (ABPM) was conducted on 166 patients. ABPM was conducted at baseline and at Day 139 of therapy. A total of 135 patients had acceptable ABPM recordings at both time periods. In that group, the mean change in 24-hour systolic blood pressure and diastolic blood pressure from baseline to final on-treatment visit on Day 139 (n=135) was 4.9 mmHg (95% CI 3.5, 6.4) and 2.5 mmHg (95% CI 1.5, 3.6), respectively.

The ABPM systolic and diastolic increases were larger in patients with a history of hypertension who were being treated with antihypertensive therapy (5.4 mmHg [95% CI 3.3, 7.6] and 3.2 mmHg [95% CI 1.7, 4.7], respectively [n=67]) compared to patients with no history of hypertension at baseline (4.4 mmHg [95% CI 2.3, 6.4] and 1.8 mmHg [95% CI 0.2, 3.3], respectively [n=63]).

The blood pressure measured in a clinic setting using blood pressure cuff measurements rose during the course of treatment with a mean systolic increase of 2.8 mmHg (95% CI 1.0, 4.6) and a mean diastolic increase of 0.6 mmHg (95% CI -0.7, 1.9) at the final on-treatment visit (Day 139).

Twelve (7.2%) patients started antihypertensive or had their antihypertensive regimen increased during the course of the study. A total of 6 patients were reported to have an adverse reaction of hypertension (2 patients with hypertension and 4 patients with worsening hypertension), and 3 were reported to have an adverse reaction of increased blood pressure.

Mean heart rate increased by an average of 2.2 beats per minute (bpm) [95% CI (1.0, 3.3), N=135] during the study. Patients without a history of hypertension had a greater average increase in mean heart rate (2.7 bpm [95% CI (0.8, 4.6), N=63]) compared to patients with treated hypertension (1.9 bpm [95% CI (0.3, 3.5), N=67)]).

Example 2

Clinical Trials in Hypogonadal Males

The efficacy and safety of JATENZO was evaluated in 166 adult hypogonadal males in an open label study of approximately 4 months duration (NCT02722278). The study included a Screening Phase, a Treatment Titration Phase, and a Treatment Maintenance Phase.

JATENZO was taken orally at a starting dose of 237 mg twice per day with meals. The dose was adjusted on Days 21 and 56 between a minimum of 158 mg twice per day and a maximum of 396 mg twice per day on the basis of the average testosterone concentration obtained over 24 hours post-morning dose.

The primary endpoint was the percentage of patients with mean plasma total testosterone concentration ($C_{avg}$) over 24-hours within the normal eugonadal range on the final PK visit of the study.

Secondary endpoints were the percentage of patients with a maximum total testosterone concentration (Cmax) above three predetermined limits: less than or equal to 1500 ng/dL, between 1800 and 2500 ng/dL, and greater than 2500 ng/dL.

One hundred and forty-five (87%) of the 166 hypogonadal men who received JATENZO had a mean total testosterone concentration (Cavg) within the normal eugonadal range at the end of treatment.

The percentage of patients who received JATENZO and had Cmax less than or equal to 1500 ng/dL, between 1800 and 2500 ng/dL, and greater than 2500 ng/dL at the final PK visit were 83%, 3%, and 3%, respectively. Note that the testosterone concentrations were not measured in serum but the effects of different sample preparation conditions were accounted for in data analysis of the results shown here. The titration scheme for use in clinical practice is based on serum total testosterone.

Other Embodiments

The detailed description set-forth above is provided to aid those skilled in the art in practicing the present invention. However, the invention described and claimed herein is not to be limited in scope by the specific embodiments herein disclosed because these embodiments are intended as illustration of several aspects of the invention. Any equivalent embodiments are intended to be within the scope of this invention. Indeed, various modifications of the invention in addition to those shown and described herein will become apparent to those skilled in the art from the foregoing description, which do not depart from the spirit or scope of the present inventive discovery. Such modifications are also intended to fall within the scope of the appended claims.

What is claimed is:

1. A method of treating conditions associated with a deficiency or absence of endogenous testosterone in a subject in need thereof who has adequately controlled blood pressure, said method comprising:
    administering twice daily to the subject a defined dose of an oral pharmaceutical composition comprising about 15-20 percent by weight of solubilized testosterone undecanoate, about 5-20 percent by weight of hydrophilic surfactant, about 50-70 percent by weight of lipophilic surfactant which is a fatty acid; and about 10-15 percent by weight of digestible oil,
    wherein said oral pharmaceutical composition exhibits a percent (%) in vitro dissolution profile in 5% TRITON X-100 (Polyethylene glycol tert-octylphenyl ether) solution in phosphate buffer, pH 6.8, indicating release from the composition of substantially all of the solubilized testosterone undecanoate within about 2 hours.

2. The method of claim 1, wherein the subject is not being treated with antihypertensive therapy.

3. The method of claim 1, wherein the subject is being treated with antihypertensive therapy.

4. The method of claim 1, wherein the subject does not have a history of hypertension.

5. The method of claim 1, wherein the subject has a history of hypertension.

6. The method of claim 1, further comprising:
    administering twice daily for approximately three weeks to the subject the defined dose of the oral pharmaceutical composition;
    monitoring the subject for new-onset hypertension or exacerbation of pre-existing hypertension; and
    treating the subject for new-onset hypertension or exacerbation of pre-existing hypertension.

7. The method of claim 1, further comprising:
    administering twice daily to the subject an increased dose of the oral pharmaceutical composition;
    monitoring the subject for new-onset hypertension or exacerbation of pre-existing hypertension; and
    treating the subject for new-onset hypertension or exacerbation of pre-existing hypertension.

8. The method of claim 1, wherein the subject is diagnosed with hypogonadal conditions associated with structural or genetic etiologies.

9. The method of claim 1, wherein the subject is diagnosed with primary hypogonadism.

10. The method of claim 9, wherein the subject is diagnosed with testicular failure due to cryptorchidism, bilateral torsion, orchitis, vanishing testis syndrome, orchiectomy, Klinefelter syndrome, chemotherapy, or toxic damage from alcohol or heavy metals.

11. The method of claim 1, wherein the subject is diagnosed with hypogonadotropic hypogonadism.

12. The method of claim 11, wherein the subject is diagnosed with gonadotropin or luteinizing hormone-releasing hormone (LHRH) deficiency or pituitary-hypothalamic injury from tumors, trauma, or radiation.

13. The method of claim 1, wherein the subject is not diagnosed with age-related hypogonadism.

14. The method of claim 1, further comprising informing the subject that administration of the oral pharmaceutical composition may result in an increase in blood pressure.

15. The method of claim 14, wherein administration of the oral pharmaceutical composition results in an average increase of systolic blood pressure of 4.9 mm Hg based on ambulatory blood pressure monitoring.

16. The method of claim 14, wherein administration of the oral pharmaceutical composition results in an average increase of systolic blood pressure of 2.8 mm Hg based on blood pressure cuff measurements.

17. The method of claim 1, further comprising informing the subject that co-administration of the oral pharmaceutical composition with a prescription medication known to increase blood pressure and/or a nonprescription analgesic and/or a cold medication may result in additional increases in blood pressure.

18. The method of claim 1, further comprising monitoring the subject's blood pressure.

19. The method of claim 1, further comprising informing the subject that administration of the oral pharmaceutical composition may result in an increased risk of a major adverse cardiovascular event (MACE).

20. The method of claim 1, wherein the MACE is chosen from myocardial infarction, stroke and cardiovascular death.

21. The method of claim 16, wherein the subject has one or more cardiovascular risk factors or established cardiovascular disease.

22. The method of claim 1, further comprising:
    collecting said subject's blood sample;
    measuring the serum testosterone concentration in the subject; and
    if the measured serum testosterone concentration is less than about 425 ng/dL, increasing the dose of testosterone undecanoate administered;
    if the measured serum testosterone concentration is greater than about 970 ng/dL decreasing the dose of testosterone undecanoate; and
    if the measured serum testosterone concentration is between about 425 ng/dL and about 970 ng/dL, maintaining the dose of testosterone undecanoate administered.

23. The method of claim 1, wherein the defined dose comprises about 237 mg of testosterone undecanoate.

24. The method of claim 23, wherein the dose of testosterone undecanoate is increased by about 40 mg to about 80 mg when the measured serum testosterone concentration in the subject is less than about 425 ng/dL.

25. The method of claim 23, wherein the dose of testosterone undecanoate is decreased by about 10 mg to about 40 mg when the measured serum testosterone concentration in the subject is greater than about 970 ng/dL.

26. The method of claim 22, wherein the serum testosterone concentration is measured four to eight hours after administering the oral pharmaceutical composition.

27. The method of claim 1, wherein said oral pharmaceutical composition exhibits a percent (%) in vitro dissolution profile in 5% Triton X-100 solution in phosphate buffer, pH 6.8, indicating release from the composition of substantially all of the solubilized testosterone undecanoate within about 1 hour.

* * * * *

UNITED STATES PATENT AND TRADEMARK OFFICE
CERTIFICATE OF CORRECTION

| | | |
|---|---|---|
| PATENT NO. | : 11,564,933 B2 | Page 1 of 1 |
| APPLICATION NO. | : 16/382835 | |
| DATED | : January 31, 2023 | |
| INVENTOR(S) | : Robert E. Dudley, Theodore Danoff and James A. Longstreth | |

It is certified that error appears in the above-identified patent and that said Letters Patent is hereby corrected as shown below:

On the Title Page

Item (72) Inventors, should read:
-- "(72) Inventors: Robert E. Dudley, Murfreesboro, TN (US);
                Theodore Danoff, Philadelphia, PA (US);
                James A. Longstreth, Fort Collins, CO (US)" --

Signed and Sealed this
Eighth Day of April, 2025

Coke Morgan Stewart
*Acting Director of the United States Patent and Trademark Office*